US012796680B2

(12) United States Patent
Sciortino et al.

(10) Patent No.: US 12,796,680 B2
(45) Date of Patent: Nov. 17, 2026

(54) EX-VIVO HEART PERFUSION SYSTEMS

(71) Applicants: University of Pittsburgh—Of the Commonwealth System of Higher Education, Pittsburgh, PA (US); UPMC, Pittsburgh, PA (US)

(72) Inventors: Christopher Michael Sciortino, Pittsburgh, PA (US); Sarah Burki, Pittsburgh, PA (US); Garrett N. Coyan, Pittsburgh, PA (US); Brandon D'Aloiso, Pittsburgh, PA (US)

(73) Assignees: University of Pittsburgh—Of the Commonwealth System of Higher Education, Pittsburgh, PA (US); UPMC, Pittsburgh, PA (US)

( * ) Notice: Subject to any disclaimer, the term of this patent is extended or adjusted under 35 U.S.C. 154(b) by 953 days.

(21) Appl. No.: 17/927,681

(22) PCT Filed: Jun. 10, 2021

(86) PCT No.: PCT/US2021/036744
§ 371 (c)(1),
(2) Date: Nov. 23, 2022

(87) PCT Pub. No.: WO2021/252721
PCT Pub. Date: Dec. 16, 2021

(65) Prior Publication Data

US 2023/0217916 A1 Jul. 13, 2023

Related U.S. Application Data

(60) Provisional application No. 63/037,927, filed on Jun. 11, 2020.

(51) Int. Cl.

| | |
|---|---|
| ***A01N 1/143*** | (2025.01) |
| ***A01N 1/148*** | (2025.01) |
| ***A61M 60/855*** | (2021.01) |

(52) U.S. Cl.
CPC ............ *A01N 1/143* (2025.01); *A01N 1/148* (2025.01); *A61M 60/855* (2021.01)

(58) Field of Classification Search
CPC ...... A01N 1/143; A01N 1/148; A61M 60/855
See application file for complete search history.

(56) References Cited

U.S. PATENT DOCUMENTS

| | | | | |
|---|---|---|---|---|
| 10,405,756 | B2 | 9/2019 | Steen et al. | |
| 2020/0120924 | A1* | 4/2020 | Badiwala ............... | A01N 1/143 |

OTHER PUBLICATIONS

International Search Report and Written Opinion of the International Searching Authority, mailed Oct. 5, 2021, for corresponding International Application No. PCT/US2021/036744, 8 pages.

* cited by examiner

*Primary Examiner* — Aaron J Kosar
(74) *Attorney, Agent, or Firm* — Klarquist Sparkman, LLP

(57) ABSTRACT

Disclosed herein are ex-vivo cardiac perfusion systems that can support the metabolic function of an ex-vivo heart and also have the capacity to test the functions of the heart. For example, an ex-vivo heart can be placed within and connected to a cardiac perfusion system, as disclosed herein, resuscitated and supported medically, and also tested to determine cardiac recovery. Further, these systems can also be used for research purposes to study the pressure, work, and mechanical function of many types of hearts (e.g., failed hearts that are explanted at the time of heart transplant). Some embodiments include a detachable sub-system that includes a heart chamber and components for operating in a Langendorff mode while transporting an ex-vivo heart, and the sub-system can be coupled to a differential perfusion system to form a larger, full service system for supporting, recovering, testing the heart.

12 Claims, 7 Drawing Sheets

EX-VIVO HEART PERFUSION SYSTEMS

CROSS-REFERENCE TO RELATED APPLICATIONS

This is the U.S. National Stage of International Application No. PCT/US2021/036744, filed Jun. 10, 2021, which was published in English under PCT Article 21 (2), which in turn claims the benefit of U.S. Provisional Patent Application No. 63/037,927, filed Jun. 11, 2020, which is incorporated by reference herein in its entirety.

FIELD

This application relates to systems for maintaining, supporting, rehabilitating, and testing ex-vivo hearts.

BACKGROUND

There is currently a paucity of suitable hearts for transplantation. Approximately 20% of patients listed for heart transplant will die before receiving a suitable heart. Heart allocation is a time sensitive process in which donor hearts are evaluated and allocated within 1-2 days of identification. Many hearts of otherwise healthy donors are declined due to poor cardiac function at the time of allocation. Cardiac suppression can occur at the time of brain death due to a variety of factors including trauma, cardiac stress, metabolic derangement, and prolonged cardiac arrest secondary to non-cardiac etiologies. It is well known that many of these otherwise normal hearts can recover to normal or near normal function if appropriately supported; however, this can take several days and is not typically feasible at the time of organ allocation. Therefore, many of these hearts are discarded.

Ex-vivo systems exist for the support of explanted donor hearts. However, no system exists that can adequately test the function of an ex-vivo heart. There is a need for such a system as it is imperative that functional recovery is demonstrated prior to transplantation.

SUMMARY

Disclosed herein are ex-vivo cardiac perfusion systems that can support the metabolic function of a heart and have the capacity to test the functions of a heart. For example, an ex-vivo heart can be placed within and connected to a cardiac perfusion system, as disclosed herein, resuscitated and supported medically, and then tested to determine cardiac recovery. Further, these systems can also be used for research purposes to study the pressure, work, and mechanical function of many types of hearts (e.g., failed hearts that are explanted at the time of heart transplant).

Exemplary ex-vivo heart perfusion systems can comprise: a perfusate reservoir; a pump; an oxygenator; a right atrial adaptor; a pulmonary artery adaptor; a left atrial adaptor; an aortic adaptor; a network of fluid conduits; and a plurality of valves coupled to the conduits and operable to selectively close and open perfusate flow pathways in the system.

The perfusion system can be configurable to the following modes, in part by opening and closing the valves to create different flow circuits:

(1) Langendorff Perfusion Mode, wherein perfusate is directed to coronary arteries of the heart;

(2) Isolated Left Heart Working Mode, wherein perfusate is directed to the left half of the heart;

(3) Isolated Right Heart Working Mode, wherein perfusate is directed to the right half of the heart; and (4) Whole Heart Working Mode, wherein perfusate is directed to both the left and right halves of the heart. The pathway taken in this Mode mimics normal perfusate flow of the heart in the human body.

The system can further comprise additional components and subsystems, such as any of the following: a housing that comprises an organ chamber that holds and contains the heart, a pace setting system comprising electrical leads configured to control contractile rhythm of the heart, an operator interface to communicate with and control various components and properties of the system, an environmental control system that maintains desired conditions around the heart, flow rate sensors and pressure sensors coupled to the conduits, and/or other complementary components.

In some embodiments, the aortic adaptor comprises an aortic inlet, an aortic outlet, and a Langendorff inlet port, wherein the Langendorff inlet port allows a reduced flow of perfusate to reach the coronary arteries from the aorta.

Some exemplary ex-vivo heart perfusion systems comprise a portable sub-system that is coupled to and detachable from a differential perfusion circuit. The portable sub-system can comprise at least an enclosure configured to receive an ex-vivo heart from a donor, an aortic adaptor that is fluidly couplable to an aorta of the heart, a reservoir that contains a volume of perfusate, a pump that pumps the perfusate through the sub-system, and conduits that fluidly couple the reservoir, the pump, and the aortic adaptor, wherein the sub-system is operable in a Langendorff Perfusion Mode where perfusate is directed from the reservoir to the aortic adaptor, and from the aortic adaptor through the aorta into coronary arteries of the heart. The differential perfusion system can comprise at least a left heart circuit, a right heart circuit, and connectors for coupling the left heart circuit and right heart circuit to the sub-system. The sub-system is operable to transport the ex-vivo heart from the donor to the differential perfusion system while operating in the Langendorff Perfusion Mode, the sub-system is coupleable to the differential perfusion system via the connectors without decoupling the heart from the sub-system, and when the sub-system is coupled to the differential perfusion system, the ex-vivo heart perfusion system is operable to function in Isolated Left Heart Working Mode, Isolated Right Heart Working Mode, and Whole Heart Working Mode.

In some embodiments, the sub-system further comprises a right atrial adaptor configured to fluidly couple the system to a right atrium of the heart, a left atrial adaptor configured to fluidly couple the system to a left atrium of the heart, and a pulmonary artery adaptor configured to fluidly couple the system to a pulmonary artery of the heart.

In some embodiments, the sub-system further comprises a cushioning pad within the enclosure for the heart to rest against. The cushioning pad can include a space for receiving an echocardiograph (ECG) probe and the cushioning pad can be echolucent to allow imaging of the heart with the ECG probe.

In some embodiments, the enclosure comprises a door that opens to insert the heart into the sub-system and closes to form a fluid-tight seal enclosing the heart.

In some embodiments, the sub-system further comprises an oxygenator fluidly coupled to the pump.

In some embodiments, the sub-system further comprises a temperature control system to regulate the temperature of the heart within the enclosure.

The differential perfusion system can comprise a plurality of valves coupled to the left and right heart circuits, the valves being controllable to selectively close and open perfusate flow pathways in the system. In some embodiments, the left heart circuit comprises a left heart resistance component that applies a first selected flow resistance through the left heart circuit, and the right heart circuit comprises a right heart resistance component that applies a second selected flow resistance through the right heart circuit, and wherein the first and second selected flow resistances are adjustable. In some embodiments, the differential perfusion system comprises flow rate sensors and/or pressure sensors coupled to the left and right heart circuits.

The foregoing and other objects, features, and advantages of the disclosed technology will become more apparent from the following detailed description, which proceeds with reference to the accompanying figures.

DETAILED DESCRIPTION

Figure 1:
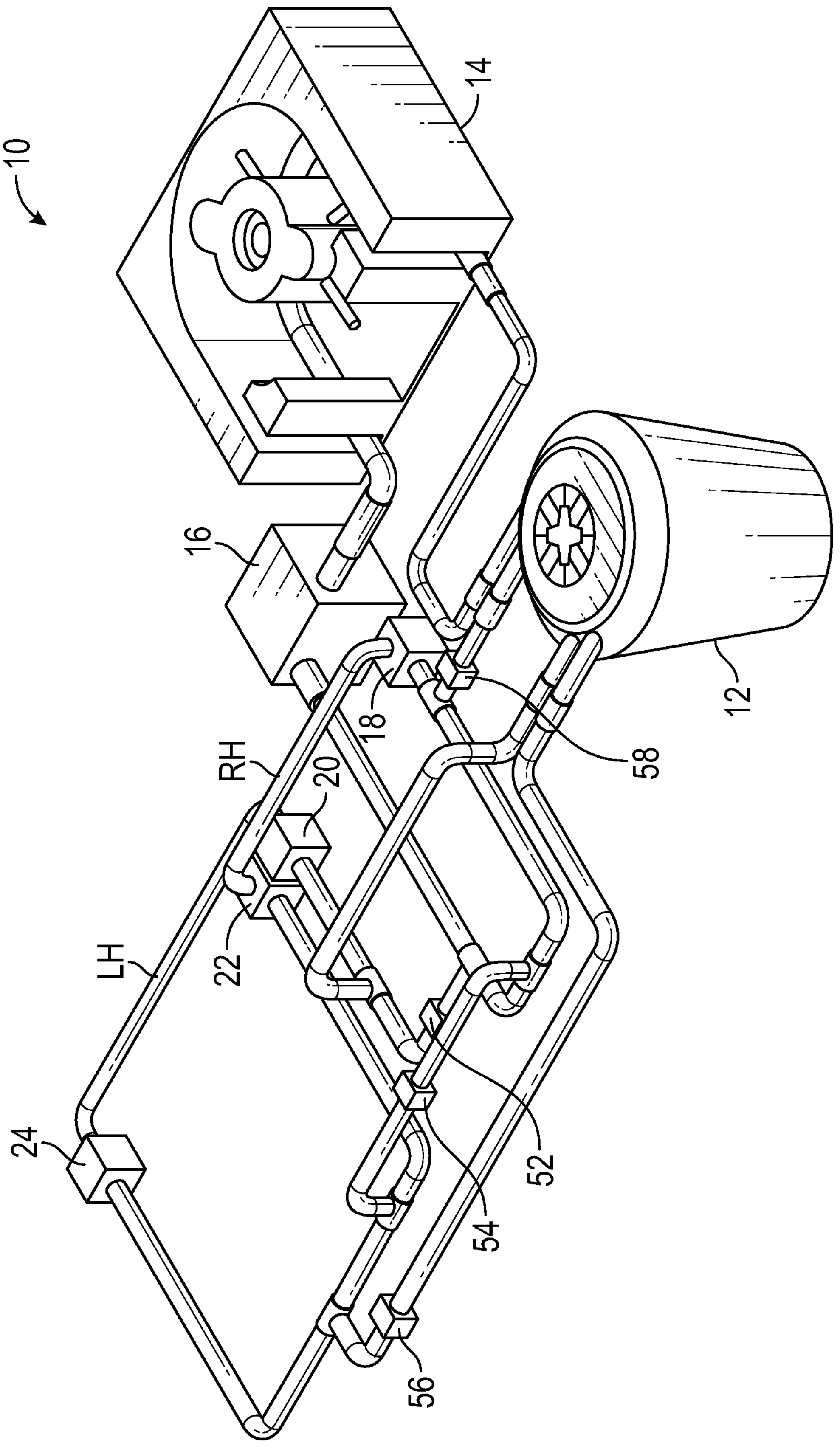
FIG. 1 shows an exemplary ex-vivo heart perfusion system that can be adjusted to create various different flow circuits with flows controlled by valves.

There currently exists no system for ex-vivo support and functional testing of human hearts. The herein described technology includes systems that incorporate a support system for an ex-vivo heart in a complex circuit for loading and functionally testing the right and left halves of a human heart separately or together, along with other functionality. This technology can facilitate explanted human hearts that are donated for transplantation, placing the hearts within the system for support and modification (e.g., cardiac recovery), and then using the ex-vivo system to volume load the heart after recovery and test the cardiac function. In doing so, hearts that are otherwise not suitable for transplantation may be able to recover in the ex-vivo system to a point where the otherwise unusable heart is suitable for transplantation, thus increasing the number of available hearts for human transplantation. The disclosed systems can also be used to study cardiac physiology of normal and failing hearts. Native hearts (failed hearts) explanted at the time of heart transplantation can be placed within this system and studied.

To support a heart, circulation can be provided in an ex-vivo fashion to deliver perfusate to the coronary arteries so that heart remains viable. The disclosed systems can be used to deliver perfusate to the coronary arteries for heart maintenance and support, and can also be used to load either the right side or the left side of the heart individually so that the functional capacity of the heart can be studied. In addition to functional testing (e.g., cardiac chamber pressure, cardiac output, etc.), the disclosed systems can be configured such that echocardiography can be performed on the ex-vivo heart to allow for structural testing as well.

The herein disclosed systems and methods can include any of the following features/capabilities:

1. Maintenance and support of a heart. This can include a perfusion and oxygenation system to maintain pressurized delivery of oxygenated perfusate and other fluids to the coronary arteries in a temperature controlled and sterile environment.
2. Pressure and flow monitoring. The system can monitor pressure at various points along the circuits (e.g., right atrial, right ventricular, pulmonary artery, left atrial, left ventricular, and/or aortic pressures). Flow probes can be placed at strategic points along the circuits to directly measure flow.
3. Differential circuits for cardiac testing. The systems can comprise two, three, four or more perfusion circuits, which can be used for:
    a. Basic coronary perfusion (Langendorff). Oxygenated perfusate is delivered directly to the coronary arteries via the aorta when the heart is completely unloaded (not performing work). Effluent perfusate is captured and returned to the circuit.
    b. Complete heart loading (full cardiac work). Oxygenated perfusate is delivered to the right atrium at a set pressure/volume. The perfusate flows to the right ventricle and the right ventricle pumps the perfusate across the pulmonic valve through a perfusion circuit of set resistance (e.g., set to physiological or supraphysiological pulmonary vascular resistance) and this perfusate is then delivered to the left atrium. The left atrial perfusate passes to the left ventricle, and the left ventricle pumps the perfusate through the circuit (e.g., set to physiological or supraphysiological systemic vascular resistance), back to the reservoir.
    c. Right heart loading. Perfusate is continuously delivered to the coronary arteries by the device for heart maintenance and support. Additionally, the circuit delivers perfusate to the right atrium at a set pressure for right heart volume loading. The right ventricle then pumps the perfusate across the conduits (e.g., at a set resistance) and then is drained to the reservoir. The left heart remains unloaded during this process.
    d. Left heart loading. Oxygenated perfusate is delivered to the left atrium which fills the left ventricle which ejects the perfusate through the aorta, then circuit and back to the reservoir. The right heart remains unloaded during this process. Perfusate fills the coronary arteries passively via the aorta.
4. Environmental control. The heart can be placed within a temperature controlled chamber that provides a sterile and safe environment. The chamber can also be controlled for pressure, humidity, gas concentrations, and/or other properties. In some embodiments, the heart can sit on a cushioned platform, such as a fluid filled platform, to minimize the risk of trauma. This fluid filled platform can contain sterile saline, for example. Adjacent to the platform can be a space for an echocardiography probe, or the like, that can be used to evaluate the structural components of the ex-vivo heart. The chamber can also include lighting, sensors, an access door, a display screen, user interface controls, and/or other features.

5. Sample retrieval and medication administration. The system can have conduits in place for the removal of circuit perfusate for laboratory testing and for the administration of cardiac support and other medications.
6. Cardiac pacemaker. Epicardial pacemaker leads can be attached to the heart at the time of placement within the system. These leads can be attached to a pacemaker box to allow for pacer control of heart rate.

Description of Exemplary Systems and Methods

Perfusion systems can include a closed loop perfusion circuit designed to facilitate ex-vivo heart physiological testing, support, and potential rehabilitation during transport. Ex-vivo heart perfusion (EVHP) as a method of donor heart preservation has recently gained interest as an alternative to the status quo. Currently, the primary method of ex-vivo heart preservation is static cold storage, whereby the organ is cooled to around 4° C. and transported in an insulated container. This method, although simple and inexpensive, has certain significant drawbacks—First, it imposes a 4-hour time limit on organ viability due to persistent organ hypometabolism in the setting of ischemia; second, subsequent rewarming and reperfusion injury imparts a risk of organ dysfunction in-vivo; finally, considering that the heart is a highly dynamic organ, there may be no visual indication of organ damage. EVHP addresses all three aspects by allowing early re-institution of oxygen- and nutrient-rich organ perfusion at body temperature. As a result, transport time may be significantly increased (e.g., up to 16 hours). Ex-vivo heart perfusions systems can enable the subject organ to maintain normothermic metabolism and allow assessment capabilities, therefore reducing the risk of transplantation failure.

The disclosed EVHP systems can also be used to treat, condition, and recover an ex-vivo heart. An ex-vivo heart may be placed in the EVHP system and allowed to rest, treated with pharmaceutical agents or substances, and/or conditioned over a period of time (e.g., several hours or days) to improve its functionality. This can result in an otherwise insufficiently healthy heart being improved to a state where it is now sufficiently healthy and viable enough to be implanted in a patient. Without such conditioning and recovery, many explanted hearts would not be able to be implanted in a patient and may need to be discarded.

Perfusion systems can comprise various components to contain, modify, and direct blood and/or other perfusion fluids (collectively referred to a perfusate). System components can include any combination of the following: a housing, an organ chamber to hold and contain the subject ex-vivo heart, a platform or other contact surface for the heart to rest on or in, a perfusate reservoir unit to contain a volume of the perfusate, flow conduits that fluidly couple the heart and to the other components, a perfusion fluid pump to circulate the perfusate through the heart and circuits, valves and clamps to open and close flow paths, flow resistors to modulate resistance to perfusate outflow from the heart (e.g., from the aorta and pulmonary artery), flow and pressure monitors in inlets (e.g., aorta in Langendorff mode, left and right atria in working mode) and outlets (e.g., pulmonary artery in Langendorff mode, aorta and pulmonary artery in working mode), heaters and coolers to control perfusate temperature, a myocardial temperature probe, a hemoconcentrator to control concentration of various blood components (in case of blood-based perfusate), an oxygenator to maintain normoxia (in case of blood-based perfusate), pacing cables to maintain a desired heart rate (e.g., 60 bpm to 200 bpm) via electrical signals, an operator interface to communicate with and control the various components in maintaining a physiological environment, and a power source (battery and/or power cord). These components can be interconnected using conduits, such as perfusion grade tubing (e.g., with internal diameters varying between ¼" and ½"), with straight and Y connectors (with or without Luer Lock ports depending on location).

Specialized connecting adaptors can be used to connect the heart to the perfusion system. An aortic adaptor can have a side port (Langendorff inlet port), which for example can accommodate a flow rate between 250 mL/min to 1 L/min, while the outlet of the aortic adaptor can accommodate a flow of, for example, up to 5 L/min. The pulmonary artery and atrial adaptors can similarly be specially designed, e.g. to accommodate a flow of up to 5 L/min.

In some embodiments, the perfusion system can include a housing that includes a door to access the organ chamber. The door can be opened to place a heart into the organ chamber and connect the heart to the tubing via aforementioned specialized adaptors. The door can be closed to seal the heart within the organ chamber so that the environment inside the organ chamber can be controlled and maintained as desired. The system can include a user interface on the outside of the housing that includes an interactive display, buttons, dials, etc., for the user to control and adjust the system. The size of system including the housing can vary, and in some embodiments can be about the size of a small refrigerator or ice box, e.g., 0.5 m tall, 0.5 m wide, and 0.5 m deep. The system can include HVAC systems, such a temperature control system, a pressure control system, a humidity control system, an air filtration system, etc. The system can further comprise a lighting system to illuminate the organ chamber. The system can further comprise a pace setting system that includes leads that are coupled to a heart to control the rhythm of the heart. The system can also include a computerized controller system, such as comprising a processor, memory, software, firmware, displays, wired and wireless communication devices, and/or other computing components.

The system can be used with various perfusates. The perfusates can comprise any combination of blood, blood components such as plasma, plasma substitutes, plasma proteins, buffers, crystalloid solutions, fluorocarbons, isotonic solutions, saline solutions, cardioplegia, drugs, nutrients, and/or other substances.

FIG. 1 illustrates an exemplary ex-vivo heart perfusion system 10. The system 10 can comprise a perfusate reservoir 12, a perfusate pump 14, an oxygenator 16, a right atrial adaptor 18, a pulmonary artery adaptor 22, a left atrial adaptor 24, an aortic adaptor 20, and various fluid conduits coupling the components together. The adaptors 18, 20, 22, 24 schematically represent structures that couple to a subject ex-vivo heart. The conduit connecting 18 to 22 schematically represents the flow path through the right side of the subject ex-vivo heart (e.g., from the right atrium, through the right ventricle, to the pulmonary artery). The conduit connecting 24 to 20 schematically represents the flow path through the left side of the subject ex-vivo heart (e.g., from the left atrium, through the left ventricle, to the aorta).

Valves can be positioned at various points along the conduits to selectively open and close the conduits, which allows for various different flow circuits to be formed. FIGS. 1-4 illustrates four different exemplary flow circuits. The structure and arrangement of the various components as shown in FIGS. 1-4 is just one example that is presented for illustrative purposes. In different embodiments, the various components can be arranged and oriented in any manner that allows the adaptors 18, 20, 22, 24 to coupled to a subject ex-vivo heart and for the system to perfuse the heart. For example, the reservoir 12, pump 14, and oxygenator 16 can have any suitable size and shape, and they can be arranged in any 3D configuration such that the perfusate can flow along the illustrated path between them. In some embodiments, the oxygenator 16 can be positioned between the reservoir and pump instead of after the pump, while in other embodiments the oxygenator can be positioned in any other suitable position around the circuit. Similarly, the pump can be positioned before the reservoir in some embodiments, or at other positions around the circuit. In some embodiments, the system can include more than one reservoir, pump, and/or oxygenator. For example, a second pump can help maintain consistent pressure around the circuit. Additional components not shown in FIGS. 1-4 can also be included along the flow circuits, such as filters, temperature controllers, pressure monitors, flow probes, other gauges and sensors, etc.

In some embodiments, more than one pump can be provided at different points around the flow circuits to better control pressure levels and flow rates around the circuits. The pump(s) can comprise pulsatile pumps or continuous flow pumps, or other types of pumps. Where two or more pumps are included, the different pumps can be of different types and can also produce different pressures and flow rates.

Whole Heart Working Mode

In FIG. 1, valves (e.g., clamps or other occlusion devices) at points 52, 54, 56, and 58 are closed while other valves are open in order to configure the system in a Whole Heart Working Mode, whereby both halves of the heart are engaged together, e.g., to simulate full physiological circulation. In this mode, the perfusate fluid pump 14 pumps perfusate from the reservoir 12 along the conduits, through the oxygenator 16 (which oxygenates the perfusate), and into the right atrium via the right atrial adaptor 18. The perfusate flow rate can be gradually increased until the right atrium ejects perfusate into the right ventricle. After adequate filling, the right ventricle ejects the perfusate into the pulmonary artery and through the pulmonary artery adaptor 22, into the pulmonary artery outflow conduit, and into the left atrium through the left atrial adaptor 24. Perfusate flow continues until the left atrium ejects perfusate into the left ventricle. After adequate filling, the left ventricle can eject the perfusate into the aorta and through the aortic adaptor 20, into the aortic outflow conduit and finally draining back into the reservoir 12. In this mode, the right and left hearts function congruently, mimicking normal physiological function.

Langendorff Perfusion Mode

Figure 2:
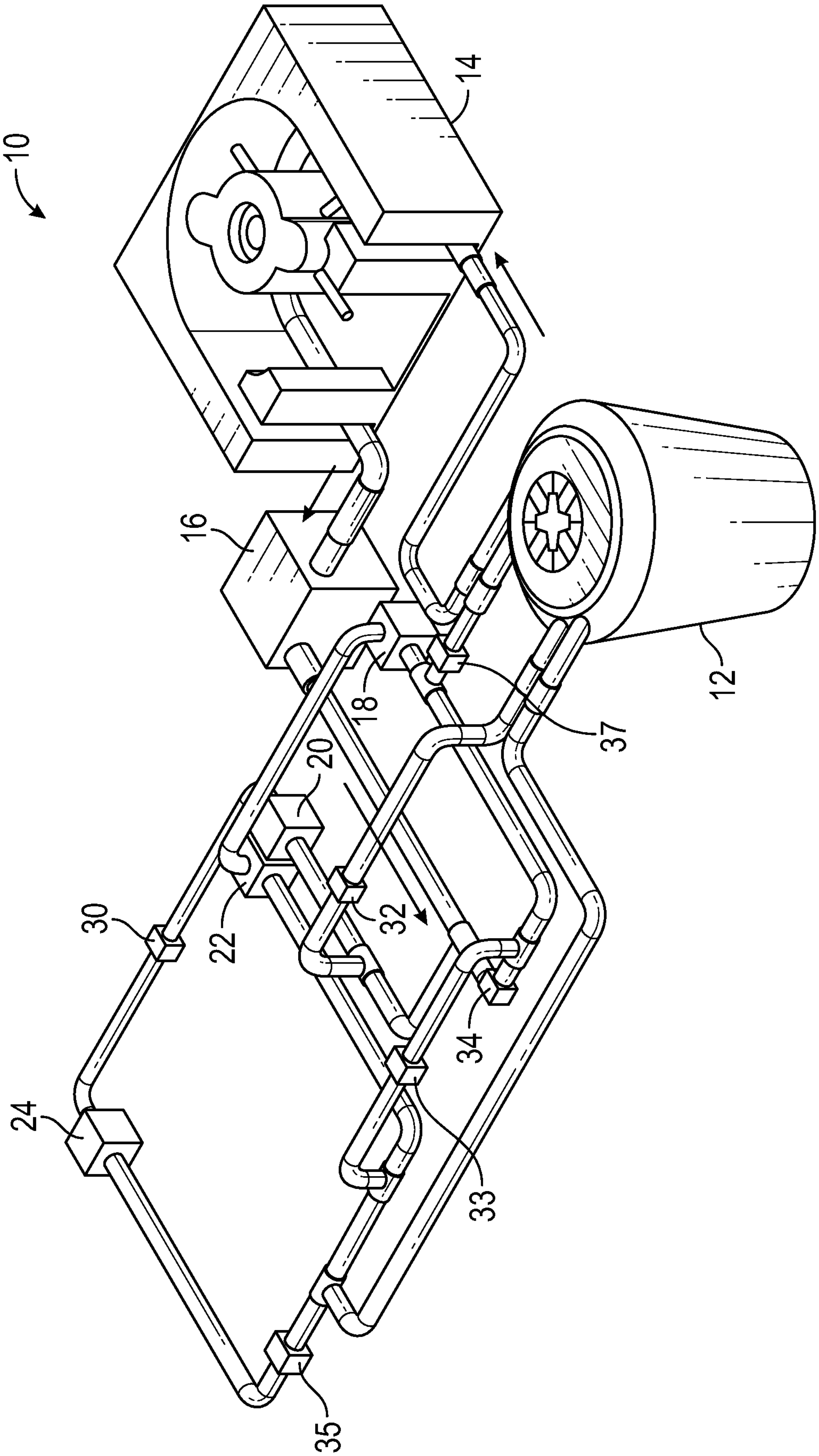
FIG. 2 illustrates a Langendorff flow circuit using the system of FIG. 1.

FIG. 2 illustrates the path of perfusate flow in a Langendorff Perfusion Mode (or Coronary Perfusion Mode). In this mode, valves at points 32, 33, 34, 35, and 37 are closed to limit the flow path. The perfusion fluid pump 14 pumps perfusate from the reservoir along the conduits, through the oxygenator 16, and into the Langendorff inlet port of the aortic adaptor 20. Perfusate then flows retrograde through the aortic adaptor into the aorta, and into the coronary arteries, perfusing the heart tissue. To facilitate sustained heart tissue perfusion, the normal antegrade aortic outflow path from the aortic adaptor 20 to the reservoir 12 can be occluded (e.g., at point 32) and retrograde flow through the left heart can be occluded via the native aortic valve and native mitral valve (represented at point 30). After perfusing the heart tissue, perfusate drains into the coronary sinus, then to the right atrium, the right ventricle and finally return to the circuit via the pulmonary artery, flowing through the pulmonary artery adaptor 22 back to the reservoir 12. The Langendorff Perfusion Mode can be continued until the heart is rewarmed, e.g. to 37C, and innate electrical activity resumes, and/or can be used to maintain the heart in the desired conditions.

Isolated Right Heart Working Mode

Figure 3:
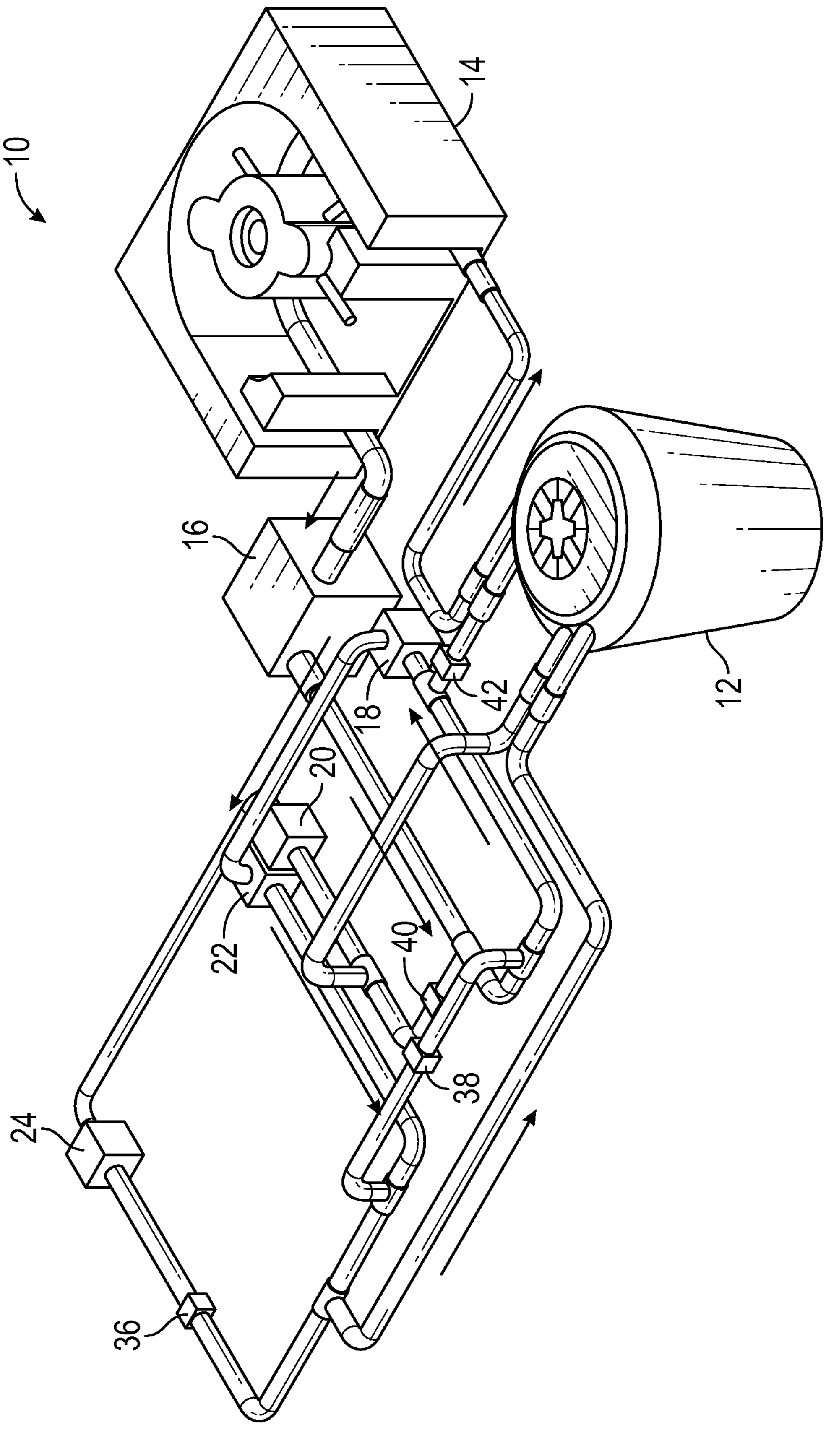
FIG. 3 illustrates a right heart flow circuit using the system of FIG. 1.

FIG. 3 illustrates the path of perfusate flow in an Isolated Right Heart Working Mode. To enact Isolated Right Heart Working Mode, perfusate flow to the left heart can be decreased to maintain coronary artery flow between 250 mL/min to 300 mL/min depending the heart's basal metabolic requirement. Using valves such as points 36, 38, 40, and 42 to restrict flow, the perfusion fluid pump 14 can pump perfusate from the reservoir 12 along the conduits, through the oxygenator 16, and into the right atrium via the right atrial adaptor 18. Perfusate flow rate can be gradually increased until the right atrium ejects perfusate into the right ventricle. After adequate filling, the right ventricle will eject the perfusate into the pulmonary artery, through the pulmonary artery adaptor 22, into the pulmonary artery outflow tubing and finally draining back into the reservoir 12. The pacing cables can continue to maintain sinus rhythm during this mode. In some examples, perfusate flow rate in this mode can be up to 5 L/min through the right heart. A method to test right ventricular contractility comprises exerting increasing resistance to pulmonary outflow, therefore mimicking increased pulmonary vascular resistance. A corresponding increase in right ventricular contractility to overcome the increased pulmonary vascular resistance can indicate ample cellular energy reserves and myocardial viability. The left heart remains unloaded during this mode.

Isolated Left Heart Working Mode

Figure 4:
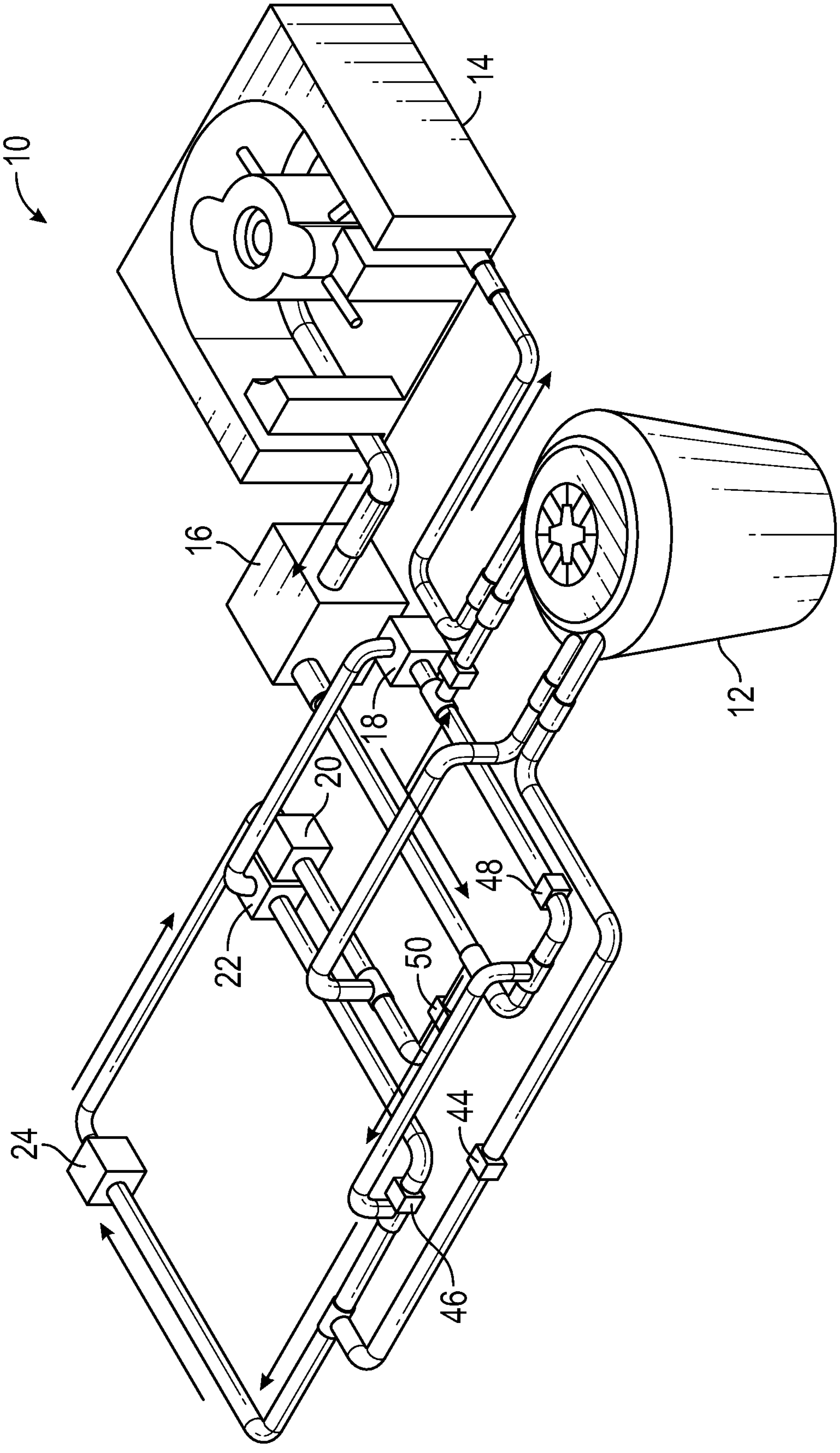
FIG. 4 illustrates a left heart flow circuit using the system of FIG. 1.

FIG. 4 illustrates the path of perfusate flow in an Isolated Left Heart Working Mode. In an exemplary method, after the heart has been appropriately resuscitated during the Langendorff Perfusion Mode (FIG. 2), the Isolated Left Heart Working Mode can be enacted. To discontinue the Langendorff Perfusion Mode, the conduit leading to the Langendorff inlet port in the aortic adaptor can be occluded (e.g., with a valve at point 50), and the conduit leading to the left atrium can be opened (e.g., opening the valve at point 35 in FIG. 2). The aortic outflow conduit can also be opened (e.g., opening the valve at point 32 in FIG. 2). Referring back to FIG. 4, using valves such as points 44, 46, 48 and 50 to restrict flow, perfusate can be circuited through the left heart. The perfusion fluid pump 14 can pump perfusate from the reservoir 12 along the conduits, through the oxygenator 16, and into the left atrium via the left atrial adaptor 24. Perfusate flow rate can be gradually increased until the left atrium ejects perfusate into the left ventricle. After adequate filling, the left ventricle can eject the perfusate into the aorta, through the aortic adaptor 20, into the aortic outflow conduit and finally draining into the 12 reservoir. Simultaneously, the pacing cables can be activated to maintain sinus rhythm. At maximum working capacity, perfusate flow rate can be approximately 5 L/min through the left heart, for example. A method to test left ventricular contractility comprises exerting increasing resistance to aortic outflow, therefore mimicking increased systemic vascular resistance. A corresponding increase in left ventricular contractility to overcome the increased systemic vascular resistance indicates ample cellular energy reserves and myocardial viability. The right heart remains unloaded during this mode.

Embodiments with Removable Sub-System

Also disclosed herein are ex-vivo heart perfusion systems that include a modular, detachable sub-system that more readily transported than the larger full system. Such a sub-system can be smaller and self-contained and more convenient to be taken to a donor heart site where a heart is explanted from a patient. The explanted heart can be placed within the sub-system and attached to conduits via adapters such that the blood or other perfusate can be provided to the ex-vivo heart within the sub-system (e.g., in a Langendorff mode) while the sub-system and ex-vivo heart are transported. The sub-system with the heart inside can then be coupled to the larger differential perfusion system (e.g., via quick-connect adaptors) that includes left and right heart circuits, such that a full array of testing, recovery, and evaluation processes can be performed. The sub-system can also be used to transport a heart from the larger full system to another location, such as to a donee patient location.

Figure 5:
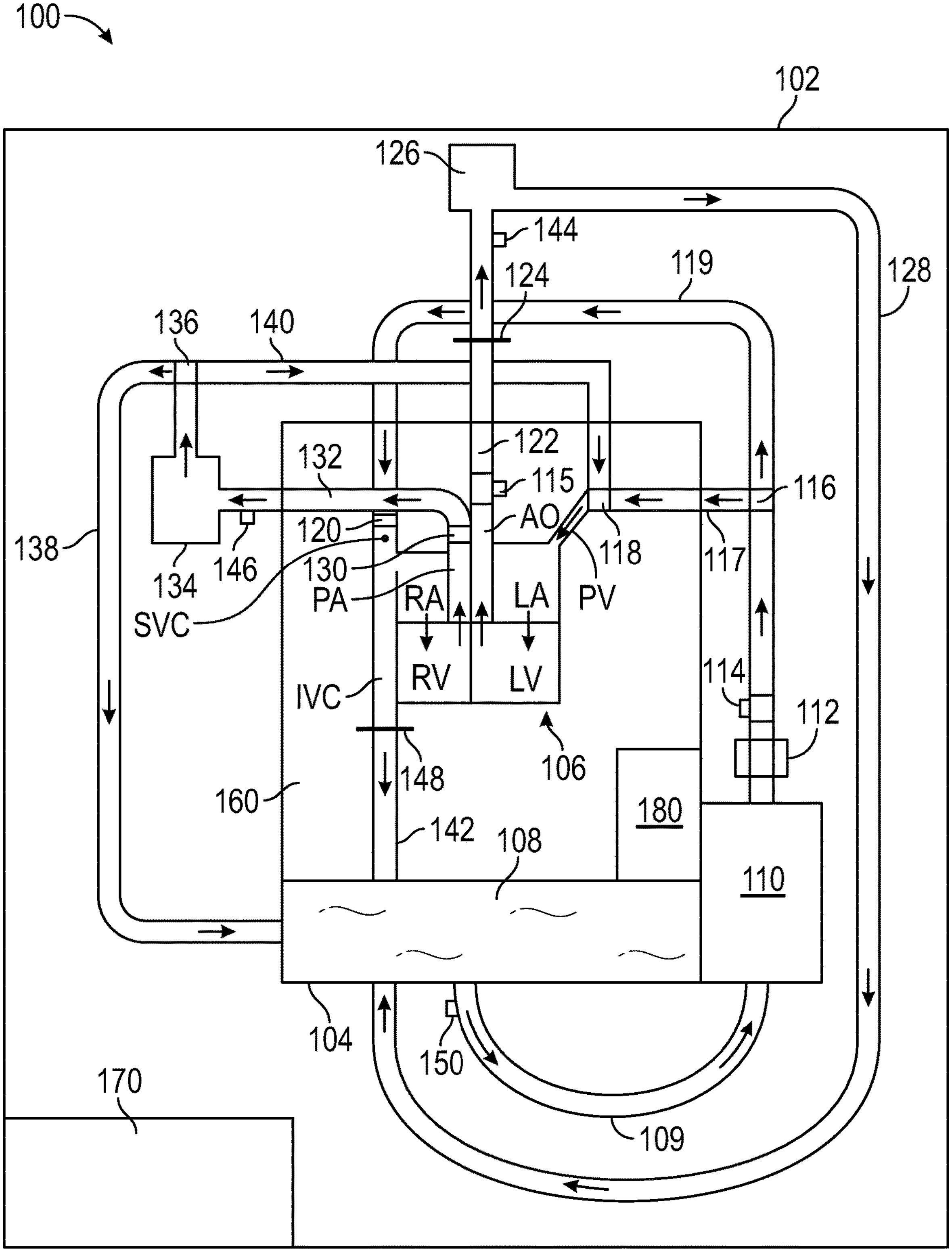
FIG. 5 illustrates another exemplary ex-vivo heart perfusion system that includes a removable sub-system that is more readily transportable.

FIG. 5 shows an exemplary ex-vivo heart perfusion system 100 that includes a differential perfusion system 102 and a sub-system 104 that is coupled to and can be detached from the differential perfusion system. An ex-vivo heart 106 is shown schematically within a chamber of the sub-system 104 attached to various conduits via adapters. The sub-system 104 includes a lower perfusate reservoir 108 and a pump 110 coupled to the reservoir via conduit 109. The sub-system can also include an oxygenator 112 coupled in-line with the pump 110. The heart 106 is coupled via the aorta (AO) to an aortic adapter 115, which can partially support the weight of the heart. The aortic adapter 115 is coupled to a conduit 122 that extends through an upper wall of the sub-system chamber and can be opened or closed via valve 124.

The differential perfusion system 102 can include a left heart circuit (including a left heart resistance component 126 and conduit 128) and a right heart circuit (including right heart resistance component 134 and conduit 138. Additional conduits, valves, sensors, and other components can also be included, as discussed below, to provide additional functionality to the differential perfusion system 102.

Perfusate from the pump 110 can pass through a T joint 114 to another T joint 116. The T joints 114 and 116 can include valves that are controllable to direct flow in one or both of two directions. The T joint 114 can be coupled to the aortic adapter 115 via a conduit that is not shown in FIG. 5 to provide flow for a Langendorff mode where perfusate is provide directly to the aorta to feed the coronary arteries. Otherwise, flow passes through the T joint 114 to the T joint 116. At the T joint 116, flow can be directed to either the left heart (e.g., for Left Heart Working Mode or Full Heart Working Mode) or to the right heart (e.g., for Right Heart Working Mode).

In Left Heart Working Mode, flow to the left heart goes from T joint 116 through conduit 117 into the organ chamber, though T joint 118, and into the left atrium (LA) via the pulmonary vein (PV). The pulmonary vein can be coupled to the conduit via an adapter. Flow then goes from the left atrium to the left ventricle, then through the aorta to the conduits 122 and 128 back to the reservoir 108. A left heart resistance component 126 can be included along conduits 122 and 128 to provide flow resistance that can approximate a natural resistance of blood flow through the body from the aorta. The resistance component 126 can comprise various forms, such as a narrowing of the conduits, one or more clamps and other impingement device that partially reduces the size of the conduits, a variable resistance device, etc. The left heart resistance component can be adjustable or variable, such that left heart resistance can be modulated, such as with electronically controlled variable in-line clamps or restrictors. The left heart pressure in conduit 122 can be monitored via a pressure sensor 144 that is electrically coupled to the control system 170.

In Right Heart Working Mode or Full Heart Working Mode, T joint 116 directs flow through conduit 119 into the right atrium (RA) via an adapter 120 coupled to the superior vena cava (SVC) as shown, and/or via the inferior vena cave (IVC). The IVC can be closed via valve 148, for example, to direct flow into the right atrium. Flow goes from the right atrium to the right ventricle and through the pulmonary artery (PA) into conduit 132 via an adapter 130. Flow can pass through a right heart resistance component 134 to a T joint 136. The right heart resistance component can simulate natural resistance provided by the lungs (which can be different from the pressure provided by the left heart resistance component). The right heart resistance component can be adjustable or variable, such that right heart resistance can be modulated, such as with variable in-line clamps or restrictors. Pressure in conduit 132 can be monitored via a pressure sensor 146 that is electrically coupled to the control system 170. In Right Heart Working Mode, the T joint 136 directs flow via conduit 138 back to the reservoir 108. In Whole Heart Working Mode, the T joint 136 directs flow via conduit 140 through T joint 118 and into the left atrium. Flow then continues through the left heart and back to the reservoir via conduits 122 and 128.

In Langendorff Perfusion Mode, flow from the pump is directed from T joint 114 to the aortic adaptor 115. With valve 124 closed, flow goes into the aorta and into the coronary arteries to feed the heart. Flow then goes through the coronary veins and drains into the right atrium, where it can flow out of the heart through the IVC to the reservoir via conduit 142.

The system 100 can also include various additional components and systems, such as a control system 170. The control system can include user interfaces for inputs and outputs, processing hardware, power supply, valve controllers, sensors positioned throughout the system, temperature control devices, humidity control devices, imaging systems, metabolic analysis systems, and/or other components. The ambient air inside the organ chamber can be monitored (e.g., for temperature, humidity, etc.) separately from, and in addition to, the heart tissue itself. The heart itself can be monitored directly (e.g., for tissue temperature, oxygenation, etc.) with sensors coupled to the heart. The perfusate can also be monitored separately (e.g., for pressure, temperature, oxygenation, other gas and metabolite levels, etc.). In addition, the sub-system 104 can have its own separate control system 180 that travels with the sub-system, which can include any of the same components as the main control system 170.

In some embodiments, the sub-system 104 can also include one or more ports, such as port 150, for injecting drugs, nutrients, or other substances into the perfusate, or for adding or removing perfusate from the system.

Figure 6:
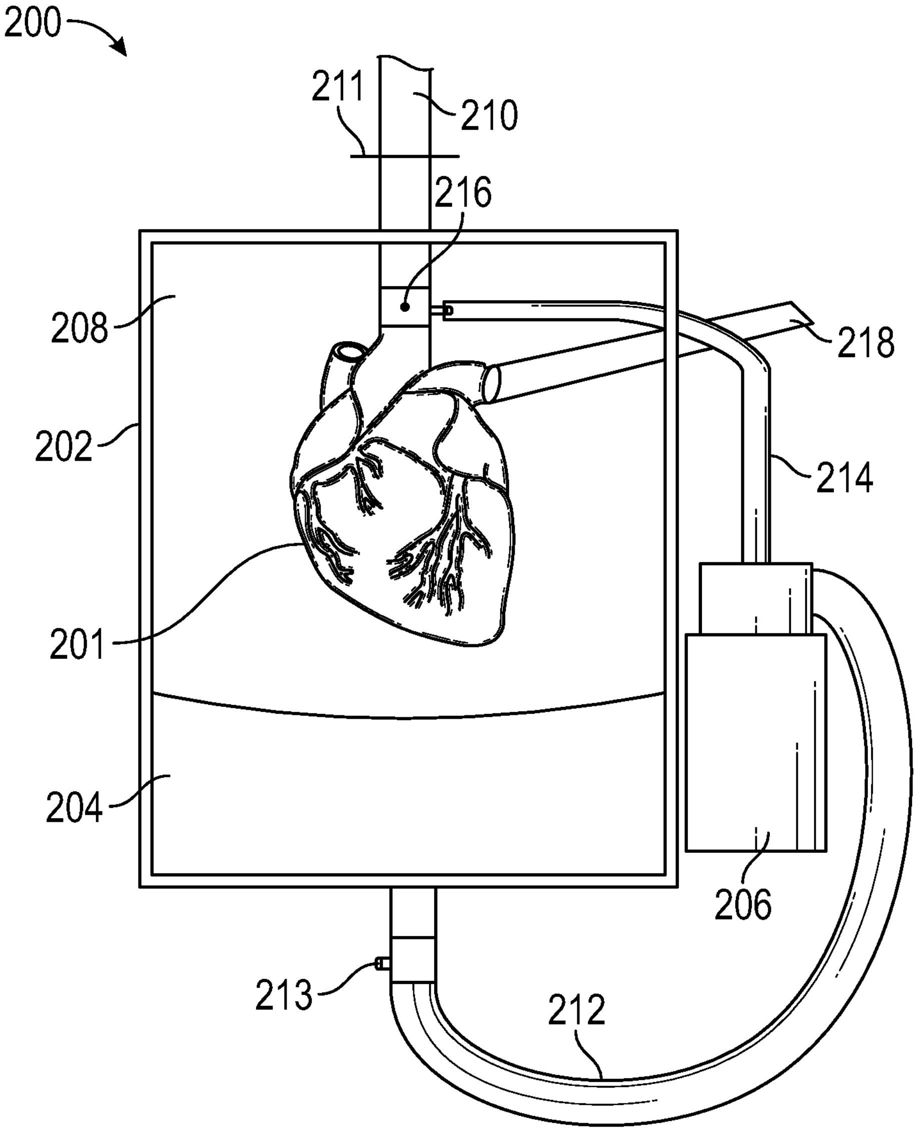
FIG. 6 is a front view of an exemplary sub-system for the system of FIG. 5.
Figure 7:
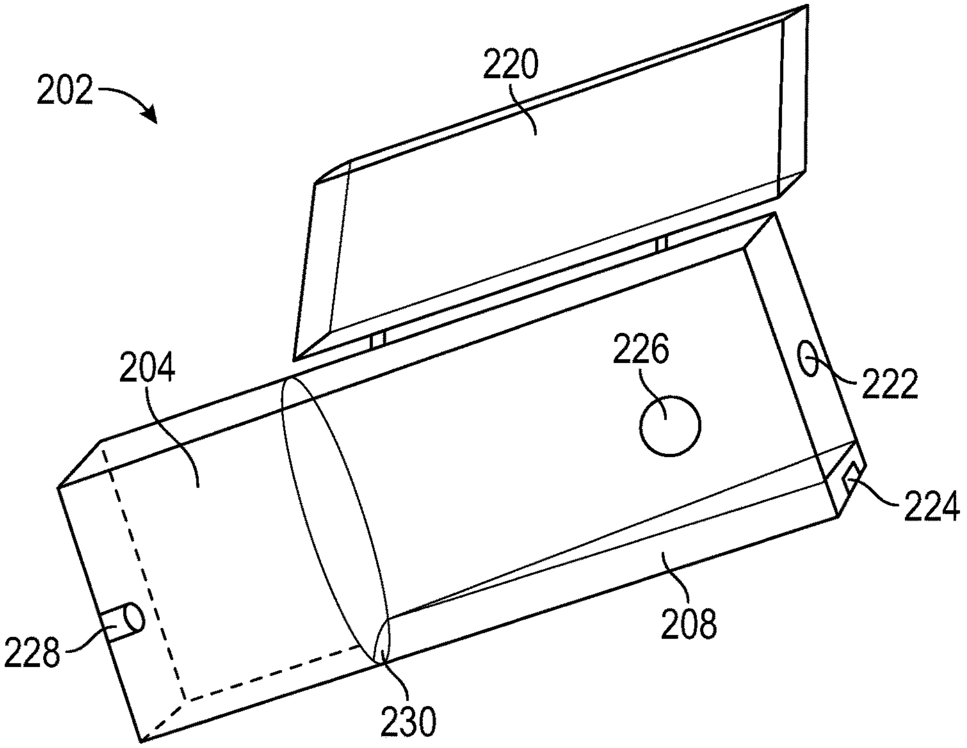
FIG. 7 is a side view of the sub-system of FIG. 6 without a heart, pump, or conduits.
Figure 8:
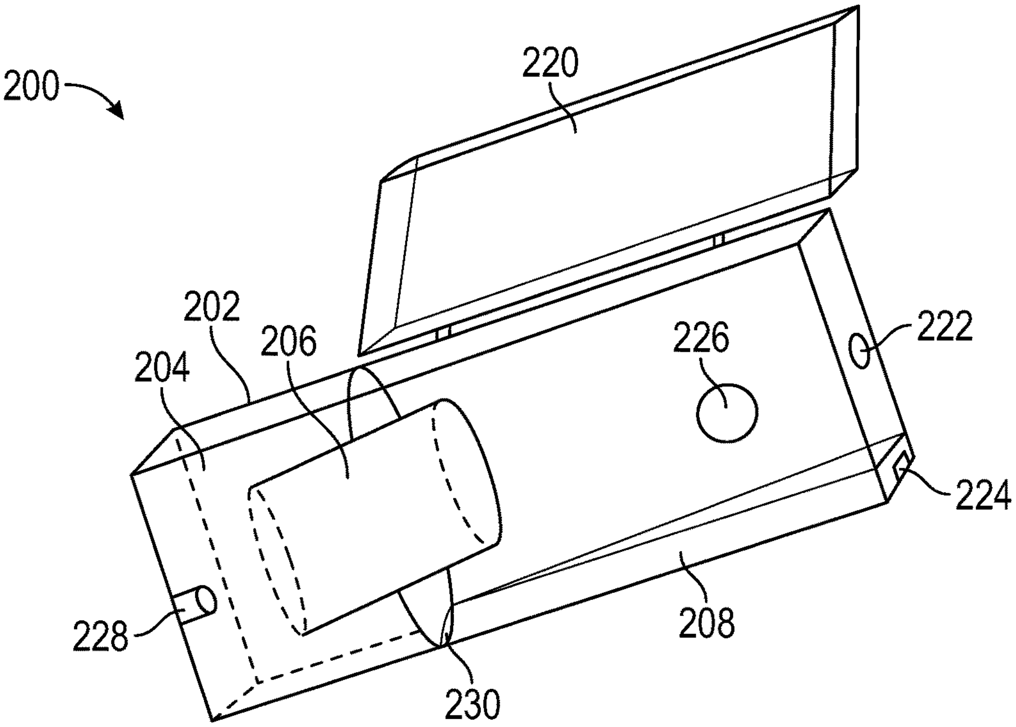
FIG. 8 is a side view of the sub-system of FIG. 7 with a pump included.

FIGS. 6-8 illustrate an exemplary sub-system 200, which can serve as the sub-system 104 of the larger system 100. Sub-system 200 is shown in a frontal view in FIG. 6 with an ex-vivo heart 201 positioned within the enclosure 202. A lower portion of the enclosure 202 comprises a reservoir 204. A pump 206 is positioned to the side of the enclosure 202 and coupled to the reservoir via conduit 212 and coupled to the aortic adaptor 216 via conduit 214. FIG. 8 shows a side view with the pump 206 alongside the enclosure 202. An upper aortic cannula 210 extends up through the enclosure via opening 222 and can be closed off via valve 211 when the sub-system is separated from the differential perfusion system 102. An opening 228 at the bottom of the reservoir allows for coupling the conduit 21. The heart 201 is partially suspended by the aortic adaptor 216 from above and can also rest on a cushioned layer 208 along the rear/lower side of the enclosure, as shown in FIG. 7. The cushion layer 208 can include a passageway 224 for an ECG probe to be inserted behind the heart. The cushion layer 208 can comprise any material that is suitably cushioning to the heart and that is also echo-lucent to accommodate the ECG probe. The enclosure 202 can have a door 220 that opens to place the heart into the enclosure and to remove the heart, and to allow for connecting and disconnecting the heart from the various adaptors inside the enclosure. When the door 220 is closed, the enclosure 202 can be hermetically sealed to protect the heart from outside factors, to control the environment around the heart, and to prevent perfusate from leaking out. The sub-system 200 can include additional adaptors and conduits that attached to the heart, including a conduit 218 that couples to the pulmonary vein and extends through an opening 226 in the side of the enclosure. The conduit 218 can couple to the T joint 118 of the differential perfusion system 102, for example. Additional conduits can be coupled to the pulmonary artery and vena cavas in some embodiments. However, only the aortic adaptor 216 connection to the aorta is needed for Langendorff Perfusion Mode to be used, and the other openings of the heart can optionally be left exposed during this mode. As shown in FIGS. 7 and 8, the perfusate exiting the heart during Langendorff perfusion (e.g., via the inferior vena cava) can flow down to the reservoir 204 via a drain opening 230 at the bottom rear of the organ chamber.

In some embodiments, the sub-system 200 can also include one or more ports, such as port 213, for injecting drugs, nutrients, or other substances into the perfusate, or for adding or removing perfusate from the system.

While the sub-system 200 is illustrated as a rectangular box that is tilted rearwardly at an angle (FIGS. 7 and 8), the sub-system can have any external shape and orientation. The tilted orientation illustrated is meant to position the heart such that it is partially supported by the cushion layer 208 while also allowing gravity to cause the perfusate exiting the heart to flow downhill to the reservoir. In some embodiments, the heart can be fully suspended by the aortic adaptor, and in other embodiments the heart can be fully supported by the cushioning layer (e.g., the cushioning layer can be horizontal or near horizontal). Various other contoured shapes can be provided for the cushioning layer in other embodiments to more fully cradle and support the heart. Other supporting devices can also be included within the chamber.

In use, the sub-system 104/200 can be detached and removed from the differential perfusion system 102 and taken to the location where a heart is to be removed from a patient. The removed heart can be placed inside the enclosure 202 and coupled to the one or more adaptors within, and the door is closed. The heart can be coupled to the adaptors via clamps, zip-ties, sewing, or other ways. Once the heart is coupled to the connectors and the door is closed, the sub-system can begin Langendorff Perfusion Mode to supply perfusate to the coronary arteries. The perfusate can comprise blood from the heart donor, for example, organ preservation solutions, or any other suitable blood product, mixture, or other perfusate. The perfusate can be pre-oxygenated. The sub-system can include a sufficient volume of pre-oxygenated perfusate to keep the heart viable for several hours (e.g., 500 to 1000 ml). In some embodiments, the sub-system can include an oxygenator as well. The sub-system can also include a warming/cooling system to keep the heart warm (e.g., near normal body temperature) within the enclosure. Altogether, the sub-system can be configured to maintain the heart long enough for the sub-system to be transported back to the differential perfusion system 102, where it can be couple to the rest of the perfusion components to provide a full spectrum of maintenance, testing, treatment, and recovery processes for the ex-vivo heart, as described elsewhere herein. The sub-system can be inserted into, or otherwise coupled to, the differential perfusion system 102 without removing the heart from the sub-system, and without stopping the Langendorff perfusion process. This allows the door 220 to remain closed and keeps the environment within the enclosure 202 safer from disruptions, contaminations, etc.

The sub-system can also be used to transport a heart from the larger system to a donee location for implantation. The sub-system can also be used to transport a heart directly from a donor to a donee. The sub-system can also be used to temporarily store a heart for any other purpose.

In some embodiments, the ex-vivo heart perfusion systems disclosed herein can include in-line metabolic analysis systems, which can include various sensors for detecting levels of hemoglobin, lactate, myocardial enzymes (troponin, CK-MB), pH, oxygenation, CO2, electrolytes (Na, K, Cl, Bicarbonate, Mg, etc.), and/or other metabolites and other perfusate components. Such sensors and analysis systems can be included in the differential perfusion system 102 and/or in the sub-system 104/200.

In some embodiments, the differential perfusion system 102 and/or in the sub-system 104/200 can also include pacemakers/electrodes that are coupled to the heart to control the contractile rhythm of the heart.

General Considerations

Characteristics, materials, and other features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms “a”, “an”, and “at least one” encompass one or more of the specified element. That is, if two of a particular element are present, one of these elements is also present and thus “an” element is present. The terms “a plurality of” and “plural” mean two or more of the specified element. As used herein, the term “and/or” used between the last two of a list of elements means any one or more of the listed elements. For example, the phrase “A, B, and/or C” means “A”, “B,”, “C”, “A and B”, “A and C”, “B and C”, or “A, B, and C.” As used herein, the term “coupled” generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of these claims and their equivalents.

The invention claimed is:

1. An ex-vivo heart perfusion system comprising:
- a reservoir for containing a volume of perfusate;
- a pump for pumping perfusate through the system;
- an oxygenator for oxygenating the perfusate;
- a right atrial adaptor configured to fluidly couple the system to a right atrium of an ex-vivo heart;
- a pulmonary artery adaptor configured to fluidly couple the system to a pulmonary artery of the heart;
- a left atrial adaptor configured to fluidly couple the system to a left atrium of the heart;
- an aortic adaptor configured to fluidly couple the system to an aorta of the heart;
- a network of conduits that fluidly couple the reservoir, the pump, the oxygenator, the right atrial adaptor, the pulmonary artery adaptor, the left atrial adaptor, and the aortic adaptor;
- a plurality of valves coupled to the conduits and operable to selectively close and open perfusate flow pathways in the system; and
- a housing that comprises an organ chamber that holds and contains the heart, wherein the housing comprises a door that can be opened for placement and removal of the heart from the housing and closed to form a hermitically sealed environment and prevent perfusate from leaking out of the housing, wherein the housing contains the reservoir;
- wherein the system is configurable to the following modes:
  - Langendorff Perfusion Mode, wherein perfusate is directed to coronary arteries of the heart;
  - Isolated Left Heart Working Mode, wherein perfusate is directed to a left half of the heart;
  - Isolated Right Heart Working Mode, wherein perfusate is directed to a right half of the heart; and
  - Whole Heart Working Mode, wherein perfusate is directed to both the left half and the right half of the heart.

2. The system of claim 1, further comprising a pace setting system comprising electrical leads configured to control contractile rhythm of the heart.

3. The system of claim 1, further comprising an operator interface to communicate with and control various components and properties of the system.

4. The system of claim 1, further comprising an environmental control system that maintains desired conditions around the heart.

5. The system of claim 1, wherein the aortic adaptor comprises an aortic inlet, and aortic outlet, and a Langendorff inlet port.

6. The system of claim 1, wherein the system is operable to restore and maintain normothermic metabolism of the heart and to assess functional capabilities of the heart.

7. The system of claim 1, further comprising flow rate sensors coupled to the conduits.

8. The system of claim 1, wherein:
- the right atrial adaptor, the pulmonary artery adaptor, the left atrial adaptor, and the aortic adaptor are located inside the housing;
- the pump and the oxygenator are located outside the housing; and
- the network of conduits comprises a first subset of conduits that includes a first conduit and a second conduit, wherein the first conduit is in fluid communication with the reservoir and extends outside of the housing to the pump, and the second conduit extend from the pump, through an opening in the housing and to the aortic adapter.

9. The system of claim 8, wherein:
- the right atrial adaptor, the pulmonary artery adaptor, the left atrial adaptor, the aortic adaptor, the housing, the reservoir, and the first subset of conduits form a subsystem that is operable in the Langendorff Perfusion Mode;
- the network of conduits comprises a second subset of conduits that form a left heart circuit and a right heart circuit defining a differential perfusion system; and
- the sub-system is configured to be disconnected from the differential perfusion system for transporting the ex-vivo heart from a donor while operating in the Langendorff Perfusion Mode and while disconnected from the differential perfusion system, and when the sub-system is connected to the differential perfusion system, the ex-vivo perfusion system is operable in the Isolated Left Heart Working Mode, the Isolated Right Heart Working Mode, and the Whole Heart Working Mode.

10. The system of claim 1, wherein the housing contains a cushioning pad for the heart to rest against.

11. The system of claim 10, wherein the cushioning pad includes a space for receiving an echocardiograph (ECG) probe and the cushioning pad is echolucent to allow imaging of the heart with the ECG probe.

12. An ex-vivo heart perfusion system comprising:
- a reservoir for containing a volume of perfusate;
- a pump for pumping perfusate through the system;
- an oxygenator for oxygenating the perfusate;
- a right atrial adaptor configured to fluidly couple the system to a right atrium of an ex-vivo heart;
- a pulmonary artery adaptor configured to fluidly couple the system to a pulmonary artery of the heart;
- a left atrial adaptor configured to fluidly couple the system to a left atrium of the heart;
- an aortic adaptor configured to fluidly couple the system to an aorta of the heart;
- a network of conduits that fluidly couple the reservoir, the pump, the oxygenator, the right atrial adaptor, the pulmonary artery adaptor, the left atrial adaptor, and the aortic adaptor; and a plurality of valves coupled to the conduits and operable to selectively close and open perfusate flow pathways in the system;

wherein the system is configurable to the following modes:

Langendorff Perfusion Mode, wherein perfusate is directed to coronary arteries of the heart;

Isolated Left Heart Working Mode, wherein perfusate is directed to a left half of the heart;

Isolated Right Heart Working Mode, wherein perfusate is directed to a right half of the heart; and Whole Heart Working Mode, wherein perfusate is directed to both the left half and the right half of the heart;

the system further comprises pressure sensors coupled to the conduits.

* * * * *